United States Patent [19]

Amat-Larraz

[11] Patent Number: 4,898,886
[45] Date of Patent: Feb. 6, 1990

[54] UREA AGAINST ADENOCARCINOMA

[76] Inventor: Joaquin Amat-Larraz, Paseo De La Liberacion 132, Benicarlo/Castellon, Spain

[21] Appl. No.: 211,156

[22] Filed: Jun. 22, 1988

Related U.S. Application Data

[63] Continuation of Ser. No. 717,084, Mar. 28, 1985, abandoned.

[30] Foreign Application Priority Data

Mar. 28, 1984 [CH] Switzerland ............... 1563/84

[51] Int. Cl.$^4$ ............... A61K 31/17; A61K 31/34
[52] U.S. Cl. ............... 514/588; 514/474
[58] Field of Search ............... 514/588, 474

[56] References Cited

U.S. PATENT DOCUMENTS 2,840,506  6/1958  Goodfriend ............... 514/588
4,296,104  10/1981  Herschler ............... 514/588
4,424,232  1/1984  Parkinson ............... 514/588

OTHER PUBLICATIONS

Dyer, An Index of Tumor Chemotherapy, NIH, 1951, pp. 10–12 and 74.

Primary Examiner—Jerome D. Goldberg
Attorney, Agent, or Firm—Fay, Sharpe, Beall, Fagan, Minnich & McKee

[57]  ABSTRACT

This remedy against adenocarcinoma cancer contains urea in sterile water, free of pyrogenics, or in a physiological NaCl solution. The remedy may contain, additionally, ascorbic acid for better keeping quality, and sodium bicarbonate as buffer.

6 Claims, No Drawings

UREA AGAINST ADENOCARCINOMA

This is a continuation of co-pending application Ser. No. 717,084 filed on Mar. 28, 1985 now abandoned.

BACKGROUND OF THE INVENTION

This invention concerns a remedy against adenocarcinoma cancer, as well as a process for its production and its use.

One of the greatest problems in medicine today is the combating of adenocarcinoma cancer. Despite the worldwide efforts and the very high expenditures in time and financial resources, it has not been possible to solve this problem.

For the most part, malignant tumors are removed surgically today, usually by a deep intervention, in order to cut out all the diseased tissue. These interventions are often questionable, since the limit between healthy and diseased tissue is difficult to draw. In addition, these interventions also lead to a mutilation of the patient.

The radiological treating methods, which are often used after the surgical intervention, usually show unpleasant local and general side effects.

The chemotherapy used today is for the purpose of destroying adenocarcinoma cancer cells. The disadvantage of this therapy is that healthy cells are also destroyed. Moreover, experts in the field have shown (see, for example, Chemotherapeut, Muntoni), that all of the adenocarcinoma cancer cells are never destroyed, but rather, a number always remain, from which the tumor may again be formed. The other disadvantage of the known chemotherapy are the side effects, such as, for example, weakening of the patient, loss of resistance forces, poor blood, irritating rashes and a fallout of hair.

It is true that through the conventional methods, a portion of the patients are healed, since in the statistics, survival for five years is called healing. But the recurrence of the tumor after six to eight years, that is, in statistically healed cases, is more frequent all the time.

There is a greater chance of healing when the adenocarcinoma cancer can be diagnosed very early, if possible, in the preclinical stage, that is, before the appearance of any kind of symptoms. Because of the high costs, however, such investigations are limited only to limited population groups at high risk.

All these therapeutic measures in the battle against adenocarcinoma cancer are based on the assumption of an abnormal increase of cells, that is, on the increasing growth of tissues in the form of monster cells, which grow into all the surrounding tissue, and by a physiological route (blood, lymph, etc.) migrate into other parts of the human body and finally cause death. All the known measures have for their purpose the destruction of adenocarcinoma cancer cells, based on the assumption that it is a matter of bad cells. But the reasons for the deficiency of function of the community of cells should be investigated, rather, so that the community of cells can exist harmoniously and the tumors cannot be formed. Based on this consideration, the applicant has developed the following theory as to the formation of adenocarcinoma cancer, and its prevention. The subject of the present patent application is based on this theory.

Multi-cell organisms are symbiotic communities of cells with the purpose of assuring survival, that is, the continuity of themselves and their posterity. Their survival is obtained through the differentiation of cells.

One example of the effort of cells to survive is the inflammation mechanism. When a cell group is attacked by foreign enemies, leucocytes are mobilized, in order to digest the foreign substances. As a result there is an inflammation which can sometimes lead, for example, to the closing of an air tube and thus, to the death of the person, that is, of the whole organism as well as the foreign enemies which had stimulated to inflammation process.

In the case of adenocarcinoma cancer, on the other hand, it is not a matter of a foreign or harmful effect, which has penetrated into the cell structure. Consequently, the adenocarcinoma cancer is not automatically discovered, eliminated or encapsulated. In adenocarcinoma cancer, the harmful foreign enemy is the diseased cells themselves, against which no defense can exist. The adenocarcinoma cancerous agent maintains the respiration and nutrition functions of infected cells, allowing the existence and increase of this kind of cell. All the cell groups work together, so that the adenocarcinoma cancerous cells will survive, even at the cost of the cell structure itself.

The adenocarcinoma cancer may be considered a new biological condition, a reaction to something. When all the cells of a certain, probably great, group of cells are attacked, up to the moment at which their function fails, the rest of the community of cells cannot allow this death of cells or necrosis, since it would be the community's own death. There are no other cells which take over their function, and so it is decided to replace this group, that tissue, by a newly-formed one, the increase in cells being driven forward in any way and at great speed. So the tumor is formed.

The adenocarcinoma tumor results at one place, but it is like the tip of the iceberg; it is a reaction of substitution, a filling of the ecological niche of the cells which are dead or cannot perform their function. Thus, the above-mentioned cell group has failed in its symbiotic function and it must be replaced.

There is a cell disease, the disease of adenocarcinoma cancer, and there exists a biological reaction, the tumor, which, in its growth, penetrates into structures necessary to life, for example, into the liver or lungs. The tumor, therefore, does not kill, per se; rather, it kills because it takes up space.

An isolated cell is able to live in a hostile environment. The reactions to all possible events are engraved into its genetic framework. It can adapt its intimate functioning to emergency situations, in order to survive. It can live, for example, in environments very rich in glucose, without elementary oxygen, and then change its substance exchange so that it can adapt itself for the condition of so-called anaerobiosis, and in this way can obtain oxygen from the glucose. A bacterium, which, after all, is a very simple cell, can live in glucose or levulose, and in each case it retards or releases a certain enzyme for this substance exchange. There is a demonstrated theory, that of enzymatic inhibition, according to which one cell is apparently capable of synthesizing millions of enzymes. But these enzymes are inhibited, and may be disinhibited in an emergency case, and act so that they exert a different substance exchange on cell, which can adapt the cell to the new emergency situation; that is, the cell can then live in an unsuitable medium.

All the cells of one histological group function under the same conditions, (temperature, pH, etc.) which the organism dictates. When, for any reason, a more or less great group is changed as a result of hostile conditions, it will no longer fulfill its function. Therefore, other cells must fulfill this function through a hyper-function. Some U.S. researchers, after the discovery of oncogenesis, pointed to the possibility that this reaction is engraved in the genetic code.

A young organism, however, can regulate cell malfunctions which result, through its own defense mechanisms. When an organism can no longer do this, that is, when the regulation, adaptation and compensation mechanisms fail, it is a matter of a great malfunction of a large zone of the organism, and therefore an adenocarcinoma cancer which, despite strong mechanisms, is not regulatable. The tumors are less frequent, therefore, in young people, but more severe or more malignant than in their elders. In older people, on the other hand, malfunctions of small groups cannot be controlled or compensated, since the mechanisms for this have been exhausted. They trigger a tumor, which may, however, be very slow in its growth.

There exists a direct relation between tumor growth and the disease of adenocarcinoma cancer; that is the formation of a tumor is not triggered, nor a spontaneous and automatic growth. Rather, the tumor needs progressive pulses of formation; that is, it needs the existence of an adenocarcinoma cancer. If this is retarded, the tumor is retarded also. This explains the spontaneous regression of some known tumors. It is not to be assumed that after the regulation of the malfunction the tumor will automatically continue to grow.

In the investigation of true adenocarcinoma cancer, it has been found that urea plays a very important part.

Conventionally, it is assumed that urea is the end product of the protein catabolism of mammals.

The human organism is unable to use nitrogen in its strict molecular forum. Instead it must receive nitrogen in chemical compositions. The human organism is unable to synthesize amino acids from ammonia as a source of nitrogen; rather, the human organism must receive amino acids already formed in its food. With this, the organism synthesizes proteins, nucleic acids, etc. The organism can receive purine bases of pyrimidines, as well as small amounts of vitamins. Thus, humans need complex nitrogen products for their protein anabolism. There exists, therefore, in humans, a repression of those genes which are able to synthesize amino acids from ammonia.

It is also known that anabolism and catabolism occurs concurrently in the cell. Almost all metabolic reactions are connected with each other, since the product of one enzymatic reaction is transformed into the substratum of the next. Anabolism and catabolism may be based one on the other in the tricarboxylic acid cycle (also called the citric acid or krebs cycle), where the nutrients are oxidized to $CO_2$ and $H_2O$. Three characteristic phases are distinguished, of which Phase III is common to anabolism and catabolism. From the alpha-keto acids, which are the precursors of amino acids, proteins can be formed. These are aminated in Phase II by amino spender groups. Thus, alpha amino acids are formed, and in Phase I peptide chains also result.

The idea exists that substance exchange is in an unstable equilibrium in both directions, that is, catabolic and anabolic, so that end products of catabolism can change into anabolid substrates to form beginning compositions which are then finally catabolized, of which a part is lost by conversion into energy. This part must then be replaced by another contribution, that is, by feeding.

The catabolic chains spend energy for the reactions, and the anabolic chains need energy for the conversions.

As mentioned above, at the end of the tricarboxylic acid cycle, $CO_2$ and $H_2O$ are set free. The $CO_2$ is toxic to the organism and is expelled by breathing. However, all the $CO_2$ is not expelled, since a part is metabolized with the amino groups, that is, with ammonia, which can no longer be changed back to be able to participate again in the urea cycle to the cancer. This takes place in the mitochondrria, through the action of various enzymes.

It is also known that urea is split by hydrolysis into $CO_2$ and $NH_3$ so that these are the final end products of catabolism. Ammonia takes part in the urea cycle to adenocarcinoma cancer, which reacts with $CO_2$, and in the presence of the ornithine, arginine is synthesized. The amounts of ornithine are very slight and arginine is split by the action of arginase into urea and ornithine. Thus, the urea cycle to adenocarcinoma cancer is produced again. The amounts of ornithine are very slight therefore, because practically all the arginine separates into the urea.

It is known that urea remains constant in the organism, between certain limits, so that neither age nor the ingestion of proteins, etc., have any influence. Therefore, the urea cycle must have a control which regulates the formation of urea within certain limits; but if this were so, it would mean that the cyclic mechanism of ornithine-arginine, at one point, increases the amount of arginine by blocking the feed-back of urea. But this is not the case, since we know that the arginine is not accumulated; rather, all the arginine is split, with the formation of urea. If this theory were true, the participating amino groups would accumulate even before the cycle. Therefore, the control must take place at another point. It is also known that this last reaction is irreversible, biochemically.

It is further known that a part of the amino groups which form in the trans-amination, are recovered through glutamic acid, to take part again in the tricarboxylic acid cycle. Those amino groups which could not be recovered, take part in the urea cycle to adenocarcinoma cancer. If, for example, a strong catabolism exists, with formation of large amounts of amino groups through trans-amination, consequently, a large amount of urea is formed; this, for example, even in case of abundant amounts of protein in the diet. The first amino groups increase the urea constant; the rest are recovered through glutamic acid, so that, if the urea constant is reduced, on the time derivative, the trans-amination and the protein catabolism are forced. Thus, the amount of amino and carboxylic groups increases; that is, the uric acid cycle to the adenocarcinoma cancer is forced and more $CO_2$ is formed, which, with the amino groups, that is, with ammonia, leads to more urea. When the urea constant increases, the cycle is prevented; with this no more ammonia and $CO_2$ are set free, so that the urea remains constant. From these considerations, it may be concluded that the urea constant is the regulator of the tricarboxylic acid cycle, that is, of the oxidative breakdown of the basic substances; therefore, urea is the regulator of the whole metabolism, both the catabolic and the anabolic.

It is also known that high concentrations of urea prevent the oxidative phosphorylation. This takes place because the rate of catabolism of a cell is controlled, not by the concentration of nutrient elements of the medium, but rather by its particular needs in the form of ATP (adenosine triphosphate); that is, the necessary fuel is used to produce the necessary energy. But the inhibition of oxidative phosphorylation means also the inhibition of the functioning of the tricarboxylic acid cycle, where ATP is stored or formed.

As we know from the results of research, there is inhibited a dehydrogenase, bound to pyridine, known as glyceraldehyde-3-phosphate dehydrogenase, which stores energy, and to which NAD (Nicatinamide Adenine Dinucleotide) is bound. It takes part in breathing and in electron transport from the organic substrate up to $O_2$. The fact that high urea concentrations inhibit oxidative phosphorylation, shows that they inhibit the tricarboxylic acid cycle. This relation between the phosphorylation of ATP to aerobic breathing (tricarboxylic acid cycle) was first recognized by Engelhardt in the Soviet Union, but only when the tricarboxylic acid cycle was formulated in 1937 did it reach more significant clarity. Kalakr and Belitzer found, for example, that under anaerobic conditions, when the breathing was poisoned by cyanide, phosphorylation did not take place. When, on the other hand, some intermediate steps of the cycle were oxidized in muscle suspensions, the inorganic phosphate contained in the medium disappeared, and was recovered in the form of organic phosphates, for example, ATP, ADP (adenosine diphosphate), glucose-6-phosphate. But it was also found that oxidative phosphorylation was not the result of glycolysis. This was shown by the inhibition of glycolysis by fluoride. Nevertheless, phosphorylation went on. Therefore, the phosphorylation of ADP, obtained through glyceraldehyde 3-phosphate-dehydrogenase, is associated with breathing and takes over the aerobic recovery of energy. Therefore, when high urea concentrations inhibit phosphorylation, they inhibit, at the same time, through inhibition of the glyceraldehyde-3-phosphate dehydrogenase, the tricarboxylic acid cycle, but not glycolysis.

Kennedy and Lehninger discovered in 1948 that isolated mitochondria catalyze the process of oxidative phosphorylation, which is associated with the oxidation of the intermediate substances of the tricarboxylic acid cycle. In this oxidative phosphorylation, since 1949 often called phosphorylation of the breathing chain, it was shown that the energy of oxide reduction is transformed into energy of phosphate binding at three points of the chain of electronic carriers, which goes from NADH to $O_2$:

1. Oxidation of iso-citrate to alpha-ketoglutarate. ($\alpha$-Ketoglutarate.)
2. Alpha-ketoglutarate to succinyl coenzyme A. (Succinyl-CoA)
3. Maleate to oxaloacetate.

Three ATP molecules are formed in the mitochondria. This energy, according to calculations, is apparently stored in the flavoproteins and cytochromes of the breathing complex of the inner mitochondrian membrane. The mitochondria set free ATP. A great part of the total protein of the inner membrane consists of flavoproteins, cytochromes and enzymes, which are responsible for the forming of ATP's, which take part in the oxidative phosphorylation and in electronic transport, and which are a part of the connection factor $F_I$, which is responsible for oxidative phosphorylation. ADP penetrates into the mitochondria; phosphorylation takes place, the tricarboxylic acid cycle begins and the ADP is left behind. In the mitochondrian exists the breathing control of the tricarboxylic cycle. The control is by the receiver; that is, with low concentrations of ADP, the rate of breathing increases, and when all the ADP has been phosphorylated to ATP, the $O_2$ consumption is reduced to the at-rest level. When the content in ADP is high and that in ATP is low, the most $O_2$ is consumed. This is not inhibited by other substrates of the tricarboxylic acids such as pyruvate. The control of the tricarboxylic acid cycle takes place through ADP and ATP, thus through the energy storer, not through the substrate.

It has been found that most of the adenocarcinoma cancer cells accumulate considerable amounts of lactate during breathing. They are unable to reduce the pyruvate to $CO_2$ and acetyl coenzyme A, since the glycolysis of the triose phase cannot be exceeded, because the NADH produced in the oxidation phase of triose, under aerobic conditions, is re-oxidized through an exchangeable system of the glycerol phosphate. The latter is inhibited, since it has no glycerol phosphate dehydrogenase. According to Caletti and co-workers, this is totally inhibited by urea in concentrations of 2 M. The adenocarcinoma cancer cell is therefore unable to oxidize the NADH through the mitochondrial route, and it reoxidizes this through pyruvate under the influence of lactate dehydrogenase. Thus, an aerobic accumulation of lactate results.

The glycolytic enzyme and the mitochondrial system of the adenocarcinoma cancer cells are exactly the same as the normal, but the kind of integration of glycolysis and breathing seems to be different. There are examples showing that products which inhibit oxidative phosphorylation, also accumulate lactate. One example is 2,4-dinitrophenol. Between the integration of glycose and breathing many controls and synergisms are effective.

From what has been said, the synergisms of the reactions in the tricarboxylic acid cycle should be shown. The cells prefer to oxidize in the presence of $O_2$, but when the cycle is hindered in any way, the phosphorylation is inhibited also. Therefore, the mitochondrial breathing is inhibited also and lactic acid results.

The more intensively the relations between glycolysis and breathing are investigated, the clearer it becomes that the concentrations of ADP and ATP are the most important control mechanisms. Any product which inhibits phosphorylation, such as urea, also inhibits the cycle. Conversely, phosphorylation is inhibited when the cycle is inhibited. Experiments have been undertaken to show the influence of urea concentration in the control of ADP and ATP. This is the regulating control of the tricarboxylic acid cycle with breathing inhibition of the mitochondria and lactate accumulation. But this is nothing other than a control of the setting free of energy of catabolism, and the receiving of energy in anabolism, respectively; that is, the control of anabolic synergism. When high urea concentrations block the cycle, it is to be assumed that low concentrations of urea accelerate the tricarboxylic acid cycle and increase protein catabolism.

If this assumption is right, control of the non-protein substance exchange is to be traced to the maintaining of the urea constant. But control of protein substance exchange is the control of the growth of cells, their un-differentiation, of the synthesis of proteins, of nucleic acids, etc.

We should bear in mind the main regulating controls of protein synthesis and the controls which influence the un-differentiation process of the cells, that is, enzymatic induction and enzymatic repression. These consist of the increase or decrease of enzyme formation in function of a substrate or end product of the enzymatic activity. A substrate can repress a whole chain or several enzymes which are responsible for its formation. Today it is assumed that induction is rather a freeing form of repression. These enzymes are determined by three genes.

No. 1, coded for the amino acid sequence.

No. 2, coded for a protein R, known as a repressor.

No. 3 is the operator gene, which is bound to the repressor.

Normally, the structure gene cannot be transcribed, since the repressor is bound to the operator. Under certain conditions, an inductor agent is deposited on the repressor and changes it into a form which shows little or no affinity for the operator, so that the structure gene is ready for transcription. In the case of enzymes repressed by end products of biosynthesis, the regulator gene is unable to impede transcription of the structure gene, but it attains this ability when it forms a complex with the co-repressor, which is the end product of biosynthesis. This might be the case of urea and the glyceraldehyde-3-phosphate-dihydrogenase. The urea would be the co-repressor, which inhibits oxidative phosphorylation, and accumulates lactate. On the other hand, it is known that the same substrate generally inhibits several enzymatic reactions at the same time, which take part in biosynthesis. It may be assumed that urea represses other genes, which form an operon, which regulates an enzyme sequence, which influences many reactions. Therefore, not only the responsibility for setting free glyceraldehyde-3-phosphate dehydrogenase, but rather a group of enzymes also, is repressed by the same repressor. For example, the His-operon in histindine has, in all 15 genes, which are coded for 10 enzymes while there are 3 in Lac-operon.

The gene which catalyzes arginine biosynthesis is coded by genes which are situated in the chromosome. The biological and biochemical principles on which its control is based, are unknown. It is thought that urea is the repressor of this gene, while more urea would mean less arginine. Less arginine groups would go into the urea cycle, and be used in the tricarboxylic acid cycle.

The term of operator also exists for an operon which blocks the operon in combining. In eucaryotic cells the genes which specify a certain sequence of enzymes, are normally distributed in different chromosomes. Even two chains of the same protein might be induced by genes which are located in different chromosomes.

Today, in the field of cell differentiation, it is assume that all cells are available through all genes, but that in each type of cell, the majority are inactive, that is, repressed. This is based on the consideration that all cells contain the same amount of DNA.

It is difficult to associate the term of enzymatic inhibition with that of cell differentiation in vertebrates, since the cell differentiation process is not so easily reversible as the process of repression or enzymatic repression, as shown through the functionalism of the nerve cells. Namely, it is impossible to mutate the latter in any way and transform them into other cells, into kidney cells, for example. It has been shown, however, that nerve cells do not suffer adenocarcinoma cancer. Namely, the tumors of the central nervous system (C.N.S.) are tumors of the ganglion cells and not the neurons. This indicates that when the differentiation is the consequence of repression of certain operons and operon groups, there are more or less strong repression in the high organisms, which control this differentiation, and that, in the case of nerve cells, they must be permanent.

The derepression of operons must be progressive and, in each case, the operon intended for a certain use is derepressed. With continuation of cell differentiation, this must be replaced by a definite, fixed repression product. Probably these are proteins, joined with the hystions which at a definite moment are derepressed.

It has now been shown how urea can and does act as a repressor for various enzymatic reactions. One of these is glyceraldehyde dehydrogenase, which takes part in oxidating phosphorylation. It has also been shown how urea regulates the tricarboxylic acid cycle to cancer. Thus, urea is the greatest substance exchange regulator and also the regulator of the synthesis of enzymatic proteins and the cell differentiating process. High urea concentrations block phosphorylation and energy transport, as well as the catabolism of the proteins which cooperate in the tricarboxylic acid cycle.

Consequently, the anabolism or the enzymatic synthesis of the proteins would also be blocked, that is, the cell itself would be blocked and with lower urea concentrations, the cells would accelerate their catabolism and anabolism and deblock enzymes, so that the enzymatic synthesis would also be accelerated and phosphorylation increased. All the basic substances would be oxidized in this way. High urea concentrations contribute to blocking of the genes and cell differentiation; that is, to the aging of the cells. This allows one to think that urea is associated with all these processes.

Research carried out recently has shown that a protonkogen can be transformed into a onkogen, from which proceeds the synthesis of a new protein, and namely because of somatic changes in the basic form of the DNA. Now if this theory is combined with another, set up recently in England, proteins might be synthesized which, in a certain way, de-repress an oncological mechanism.

All this indicates that the term of un-differentiation, that is, the reversal of differentiation, is to be ascribed to a problem of the failure of the control mechanism, which maintains a gene repression.

It is a matter of a failure (collapse) of the anabolic synergism, based on the failure of the main control, which is urea.

It is known that urea can be used as diuretic, keratolytic, compound effective as bactericide, fertilizer and as raw material for synthetic resins. (M. Negwer, Org.-Chem. Medicines and their Synonyms, Vol. I, p. 3, 5th Edition, Akademieverlag Berlin 1978). It is also known to add urea to animal feed for ruminants (Ullmann's Encyclopedia of Technical Chemistry, Vol. 12, p. 506, 4th Edition, Verlag Chemie, Weinheim-N.Y.).

Surprisingly, however, in confirmation of the theory set forth above, it has now been found that urea can be used effectively for the treating of adenocarcinoma cancer, both in animals and in humans.

The subject of the present invention, therefore, is a remedy for adenocarcinoma cancer, which contains urea in sterile water, free of pyrogen, or in a physiological NaCl solution, a process for the production of the remedy, and the use of the remedy for the treating of the disease of adenocarcinoma cancer.

From German Patent Disclosure 2,345,917, and the equivalent Swiss Pat. No. 585,218, is known a remedy for cancer, which contains a mixture of the following compounds as active components (Swiss Pat. No. 585,219, column 14).

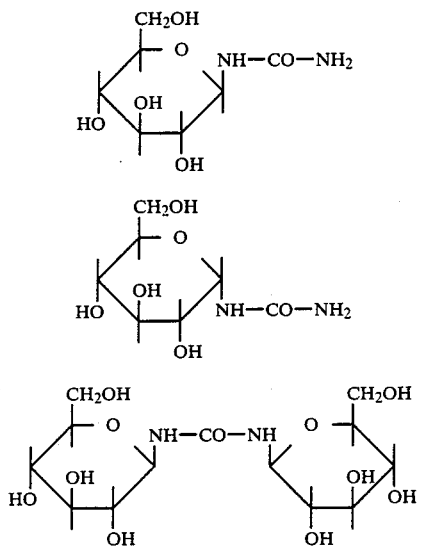

With the remedy according to German Disclosure 2,345,917 and the equivalent Swiss Pat. No. 585,219, according to the literature references, certain success has been obtained in the combatting of cancer in mice. No statement is made in the literature references about a general effectiveness of the remedy in humans. One disadvantage of this remedial agent is that the mice had to be treated with a very large amount of the active substance, namely, 0.3 to 1.7 gram per kilogram body weight, in order to obtain a result. Despite the large amount of active agent, lower healing rates were obtained in the mice than in the remedy according to the present invention. Moreover, the production of the remedial agent according to German Disclosure 2,345,971 or the equivalent Swiss Pat. No. 585,219 is costly and complicated.

With urea, in the present invention, the free, unbound compound has the formula:

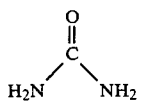

This remedy against adenocarcinoma may contain only urea, in sterile water, free of pyrogen, or in a physiological NaCl solution. The composition of NaCl solutions usable in medicine is generally known. Preferably, however, there is added to the solution a physiologically compatible acid, preferably ascorbic acid, so that the solution keeps longer and especially remains sterile. Preferably, enough ascorbic acid is used so that the pH of the solution is over 5. Instead of ascorbic acid, citric acid may also be used. It is advantageous for the medicine to contain, additionally, a physiologically compatible buffer substance, preferably a physiologically compatible bicarbonate salt. Sodium bicarbonate is especially preferred.

The urea may be contained in any desired amount, up to saturation, in the sterile water, free of pyrogen, or in the physiological NaCl solution. One preferred remedy contains 120 grams urea and 5 grams ascorbic acid or citric acid per liter physiological NaCl solution. Another preferred remedy consists of a saturated solution of urea in a physiological NaCl solution, which contains additionally 2 to 5% by weight ascorbic or citric acid and 1% by weight sodium bicarbonate, based on the total weight of the solution. A remedy which consists of 45% by weight urea, 8 to 9% by weight ascorbic acid, 1 to 2% by weight sodium bicarbonate and 45% by weight physiological NaCl solution is especially preferred.

This remedy against adenocarcinoma cancer can be prepared by dissolving urea and possibly a physiologically compatible acid, preferably ascorbic and/or a physiologically compatible bicarbonate salt, preferably sodium bicarbonate, or another buffer substance, in sterile water, free of pyrogen, or in a physiological NaCl solution. Especially preferred forms of execution of the process include dissolving 120 grams of urea and 5 grams of ascorbic acid in each liter of physiological NaCl solution. Urea can be dissolved to saturation in a physiological NaCl solution. The solution is allowed to stand for two days at 40° C. and the precipitate formed is removed. Then, based on the total weight of the solution, 2 to 5% by weight of ascorbic acid and 1% by weight of sodium bicarbonate are added to the solution. The solution is subsequently filtered.

The solution can also be prepared such that it is 45% by weight urea, 8 to 9% by weight ascorbic acid, 1 to 2% by weight sodium bicarbonate and 45% by weight physiological NaCl solution.

Below, is described, by way of example, how the remedy according to the invention can be prepared.

EXAMPLE 1

120 grams urea were dissolved in one liter physiological NaCl solution at 40° C. This was stirred from time to time. Then 5 grams ascorbic acid were added, which were also dissolved. The sterile solution was poured into sterile containers, up to 5 ml.

EXAMPLE 2

Urea was dissolved, to saturation, in a physiological NaCl solution; the solution was kept two days at 40° C. The precipitate was removed by filtration. Then 2 to 5% by weight ascorbic acid and 1% by weight sodium bicarbonate, based on the total weight of the solution, were added to the solution. The product was filtered and poured into sterile containers.

The pharmacological effectiveness of one preferred form of execution of the remedy against adenocarcinoma cancer, according to the invention was tested, in that the aszitic Carcinoma of Ehrlich (A.C.E.) in white mice was treated with a solution which consisted of 45% by weight urea, 8 to 9% by weight ascorbic acid, 1 to 2% by weight sodium bicarbonate and 45% by weight physiological NaCl solution.

The Ehrlich Carcinoma was treated in its aszitic form, choosing as an experimental animal the white mouse, Swiss strain. Chosen was an adenocarcinoma, which was obtained from a mammary tumor of the female mouse, and adapted, by repeated passages, by intraperitoneal inoculation, to the aszitic situation. The biopathology of A.C.E. is well-known. When the inoculation dose amounted to $2 \times 10^6$ cells, the period of maximum growth was established between the sixth and the tenth day. The greatest number of mitosis was established on the eighth day and the greatest number of cells on the twelfth day.

80 mice were selected, 40 female and 40 male, of equal weight, which formed two experimental groups of 40 animals each. The females received $1 \times 10^6$ cells and the males $2 \times 10^6$ cells of the A.C.E. The cells injected were prepared in PBS solution. Each mouse was marked for individual identification later.

Each of the two groups of 40 animals was divided into four subgroups of 10 animals. In each group, one of the subgroups was used as a control, while the other three subgroups were treated with 5.0, 10.0 and 15.0 mg, respectively, of the solution mentioned above, by injection. The mice treated received one injection daily.

During the experiment, some untreated control animals and some treated control animals were killed, in order to observe the tumor of the animals. The untreated animals had a tumor or a carcinoma, which was marked by the existence of asziting fluid in the abdominal cavity. Under the action of the treatment, the biopathological characteristics changed, so that in the treated animals, no Aszites resulted. Actually, in none of the killed animals were Aszites found. On the other hand, there was an enlargement of the spleen, with non-tumoral signs, and a great amount of whitish knobs, apparently of an endothelial network system nature, were found. The treated animals which were killed at the beginning of the experiment, had a solid, very well-defined tumor which rested against the skin of the abdomen and not against the abdominal organs. In microscopic observation of the treated, dissected animals, was noticeable the lower tumor growth, the less strong neoplastic invasion, the enlargement of the spleen and the non-involvement of liver, spleen, kidneys lungs, etc. The spleen was normally $2 \times 0.4$ cm. in size, with whitish, non-tumoral knobs in the parenchym. The testicles, etc., were normal. In the animals killed at the end of the experiment, everything was normal, pathologically.

The regresion and absorption process appears to be complete in a span of about two months.

From the animals killed during the experiment, to observe the turmor or carcinoma, the death dates were noted and mortality curves established. The control animals began to die after 14 days after the inoculation with the tumor cells. The last of these animals died on the nineteenth day. In the treated experimental groups there was obtained on the nineteenth and twentieth day after the inoculation, a survival rate of 80%.

We started with the inoculation of $1 \times 10^6$ and $2 \times 10^6$ tumor cells per animal; after establishing the results shown above, we increased this to $8 \times 10^6$ cells, an amount which has seldom been used up to now in oncological research; nevertheless, the results obtained were remarkable, as could be found through the survival rate (55 to 75%) and through the examination of bodies.

There seems to exist a relation between dosage and tumor; the dosage must be adapted beforehand to the pathological signs, the spreading, etc.; otherwise, the results would be poorer.

The prophylactic effect was also studied, by treating the mice at the beginning of the experiment and then ceasing treatment. The tumor developed normally. This indicates that urea shows no prophylactic effect. In very advanced stages, when the animal already has a general carcinomatosis, the regression of the damage is no longer obtained, possibly because of the organic decay caused.

If we consider the pathological findings, the survival rate, the absence of damage in those surviving, and the effect of hyperplasia of the endothelial network system, the anti-neoplastic effect of urea can be concluded without any doubt.

With the remedy against adenocarcinoma cancer, according to the invention, experiments were also carried out in pure cell cultures in chicken embryos, with human carcinoma. With cell cultures, which are prepared with a certain technique, so that no tumor strumma results, and when, of course, no endothelial network system exists, (the chicken embryo has none), an immunological reaction is impossible. A clear involution of the tumor was found, and cells in all possible involutive stages were found first, and in many cases, the tumor completely disappeared.

Groups of adenocarcinoma cancer patients in the terminal stage were treated with the adenocarcinoma cancer remedy according to the invention, in which the following results could be found:

1. Cachextic, under-nourished patients, in the final phase, in the first days of treatment, recovered their appetite and the anorexia, typical of the terminal phase in cancer patients, ceased. In many cases, a completely normal life could be led again. Many of the patients could stand walks of several kilometers.

2. In patients who had, before the beginning of the treatment, very pathological laboratory findings, there was a normalization of the latter. Red blood corpuscles, hemocrites, blood corpuscle values, etc. became normal.

The changed proteinogram (increased $\alpha$-2) etc. also became normal. The same was true of the transaminases and phosphatases. Salivary gland tumors, which were accompanied by hyperglycemia, the glucose values became normal again.

3. Pain disappeared in ¾ of the cases.

4. Bleeding hemoptysis, hematemesis, hematuria, etc. disappeared, usually with the first dose administered.

5. Discharges in any body cavity, for example, in the skin of the breast, aszites, etc. healed, often without emptying.

6. Adenocarcinoma stoppages of any of the intestinal tract, from the esophagus to the rectum, stretched and opened up under the action of the remedy according to the invention, as the prestenotic widening yielded and the function as restored. Thus indigestion (Dysphagie) with esophagal adenocarcinoma tumors disappeared. Cholestomies, in the case of intestinal adenocarcinoma tumors could also be avoided, etc. This could all be demonstrated radiologically.

7. Multiple hematogenic adenocarcinoma lung metastases sometimes disappeared completely and could no longer be shown by X-ray examination.

8. Bronchial adenocarcinoma tumors, which projected into the interior of the bronchial tubes, decreased, as could be shown by bronchoscopy, and there was even disappearance of the tumoral mass. This could all be shown through CAT scanner, planigraphy, etc.

9. Air tube adenocarcinoma tumors disappeared completely with negative anatomopthological findings, which had existed some years up to the moment of the application of the solution described herein. Thus, total or subtotal laryngectomy could be avoided.

10. Mammary adenocarcinoma tumors, diagnosed a short time ago, were pathologically negative.

Treatment of patients has shown that the remedy according to the invention is practically non-toxic and well tolerated. No undesirable side effects were found.

In further investigations, it has been found that the remedy according to the invention, containing urea, in sterile water, free of pyrogenics, or in a physiological NaCl solution, can be used with success, not only against adenocarcinoma cancer, but also against the diseases listed below. The indications of urea, unknown to now, are also the subject of the present invention.

1. Syndrome of corticorrhenal insufficiency caused by medicine and other things.
2. IMMUNOLOGICAL DEFICIENCY: Immunodeficiency Syndrome SIDA (AIDS) and congenital and acquired immunodeficiences included.
3. Cell toxicosis, infectious or not, including so-called cell toxicosis through chemical-toxic effects, for example, the toxic syndrome caused through intoxication with chemically contaminated rapeseed oil.
4. Genetic changes, both somatic and hereditary, including phenylpiruvic idiocy and others.
5. Virus diseases: Herpes of an etiology, hepatitis, infantile paralysis.
6. Bacteriostatic and bactericide.
7. Dermatological diseases, allergic or not, even those of unknown origin, leprosy, lupus, itches, hair fall.
8. Mildews, Pityriasis, athletes' foot and mycoses in general.
9. Arteriosclerosis;
10. Diabetes
11. Degenerative diseases of the C.N.S. (central nervous system), such as lateral amiotropic disease, multiple sclerosis, late syphilis, etc.; syringomyelia.
12. Rheumatological diseases of the type of rheumatoid arthritis, polyarticular (multiple joint) acute theumatism, etc., hyperuricmia (gout) included.
13. Chronic constipation.
14. Bleeding.
15. Analgesic effect.
16. Early diagnosis of adenocarcinoma cancer.
17. Diseases of the respiratory tract: allergic and non-allergic bronchial asthma;
allergic rhinitis, hay fever, choriza, chronic bronchitis, bronchiectiasis, silicosis and other occupational diseases of the respiratory tract;
emphysema, pneumonia, pneumonitis, tuberculosis, sinusitis, chronic laryngitis, chronic pharyngitis.
18. Diseases of the oral cavity: pyorrhea, caries, prophylaxis and healing of tooth fall (loose teeth).
19. Geriatrics: general tonic, slowing of aging process, improvement of quality of life in the senile.
20. Lack of appetite.
21. Hemorrhoids.
22. For scar formation in post-traumic stages, whether surgical or by accident; slow abcesses.
23. Inflammation.
24. Restoration of sexual function - impotence.
25. Gynocological diseases: bleeding, amenorrhea, dismenorrhea, leucorrhea, fibrocystic mastopathy (breast disease).
26. Multiple neurofibromatosis and other fibromasoses.
27. Benign adenocarcinoma tumors.
28. Keratolysis.
29. Lack of function of the intestinal apparatus: ulcer, hyperchlorohydria, meteroisma, atonia of the smooth muscle fibers, hypotonic stomach, ulcerous colitis.
30. Lack of function of the gall bladder and gall ducts: Cholagog, choleretic.
31. Degenerative diseases of the liver.
32. Anti-anemic, lack of iron, aplastic anemia, caused through chemical products, or other causes.
33. Allaying pruritis (itching).
34. Juvenile and other acne.
35. Acute and chronic prostatitis.
36. Neuritis and polyneuritis and other diseases of the P.N.S.
37. Burns.
38. Freezing conditions.
39. Endemic and other goiter.
40. Hyperthyroidism.
41. Hypothyroidism.

The remedy against adenocarcinoma cancer, according to the present invention is, as a rule, administered intro-muscularly, through deep intragluteal injection.

A very dilute solution of the urea in a physiological NaCl solution may also be administered intravenously, but an intra-muscular injection is preferred. Preferably, a remedy is used which consists of 45% by weight urea, 8 to 9% by weight ascorbic acid, 1 to 2% by weight sodium bicarbonate and 45% by weight physiological NaCl solution. This solution is generally injected daily, in an amount between 0.05 cc (ml) and 5 cc (ml).

I claim:

1. A method of treating animals with adenocarcinoma cancer comprising administering by injection to the affected animal an effective amount of composition comprising about 45% by weight urea, about 8% to about 9% by weight ascorbic acid, about 1% to about 2% by weight sodium bicarbonate and about 45% by weight physiological NaCl solution.
2. The method of claim 1 wherein the composition is administered intramuscularly to the area affected.
3. The method of claim 2 wherein the amount of composition administered intramuscularly to the area affected is an amount between about 0.05 cc (ml) and about 5 cc (ml).
4. The method of claim 1 wherein the composition is administered intravenously to an area affected.
5. The method of claim 4 wherein the amount of composition administered intravenously to the area affected is an amount between about 0.05 cc (ml) and about 5 cc (ml).
6. A composition for inhibiting the growth of adenocarcinoma cancer cells in animals, comprising about 45% by weight urea, about 8% to about 9% by weight ascorbic acid, about 1% to about 2% by weight sodium bicarbonate and about 45% by weight physiological NaCl solution.

* * * * *